(12) United States Patent
Giovannelli et al.

(10) Patent No.: US 10,426,914 B2
(45) Date of Patent: Oct. 1, 2019

(54) SYSTEM AND METHOD FOR ADJUSTING HUMIDIFICATION DURING PRESSURE SUPPORT THERAPY

(71) Applicant: KONINKLIJKE PHILIPS N.V., Eindhoven (NL)

(72) Inventors: Benjamin Alfred Giovannelli, Allison Park, PA (US); Jeffrey Ronald Winski, Irwin, PA (US); Mark William Dimatteo, Irwin, PA (US)

(73) Assignee: KONINKLIIKE PHILIPS N.V., Eindhoven (NL)

( * ) Notice: Subject to any disclaimer, the term of this patent is extended or adjusted under 35 U.S.C. 154(b) by 281 days.

(21) Appl. No.: 15/505,712

(22) PCT Filed: Sep. 18, 2015

(86) PCT No.: PCT/IB2015/057189
§ 371 (c)(1),
(2) Date: Feb. 22, 2017

(87) PCT Pub. No.: WO2016/042522
PCT Pub. Date: Mar. 24, 2016

(65) Prior Publication Data
US 2017/0266408 A1    Sep. 21, 2017

Related U.S. Application Data

(60) Provisional application No. 62/051,977, filed on Sep. 18, 2014.

(51) Int. Cl.
*A61M 16/16*    (2006.01)
*A61M 16/10*    (2006.01)
(Continued)

(52) U.S. Cl.
CPC .......... *A61M 16/16* (2013.01); *A61M 16/024* (2017.08); *A61M 16/1095* (2014.02);
(Continued)

(58) Field of Classification Search
CPC ............... G06F 19/3481; A61M 16/16; A61M 16/1095; A61M 16/024; A61M 16/0069;
(Continued)

(56) References Cited

U.S. PATENT DOCUMENTS 7,296,573 B2    11/2007    Estes et al.
8,453,643 B2    6/2013    Sanchez et al.
(Continued)

FOREIGN PATENT DOCUMENTS

EP        1129742 A2    9/2001
EP        2705869 A2    3/2014
(Continued)

OTHER PUBLICATIONS

Berry et al, "The Use of Auto-Titrating Continiuous Positive Airway Pressure for Treatment of Adult Obstructive Sleep Apnea", Sleep, vol. 25, No. 2, 2002, pp. 148-173.
(Continued)

*Primary Examiner* — Manuel A Mendez

(57) ABSTRACT

The present disclosure pertains to a pressure support system configured to adjust a pressurized flow of breathable gas delivered to a subject. The system is configured to simplify adjustments to humidity and/or temperature control and/or pressure support therapy that enhance the comfort level of the subject during therapy. The system is configured to generate output signals and/or determine various parameters related to the pressurized flow of breathable gas. The system is configured to receive feedback from the subject related to a comfort level of the subject during therapy and automatically adjust the pressurized flow of breathable gas and/or the
(Continued)

predetermined therapy regime, provide feedback to the subject, and/or prompt the subject to make manual adjustments based on the output signals, the determined parameters, the feedback, and/or other information.

18 Claims, 4 Drawing Sheets

(51) Int. Cl.
| | |
|---|---|
| *G06F 19/00* | (2018.01) |
| *A61M 16/00* | (2006.01) |
| *A61M 16/06* | (2006.01) |
| *A61M 16/20* | (2006.01) |

(52) U.S. Cl.
CPC ..... *G06F 19/3481* (2013.01); *A61M 16/0069* (2014.02); *A61M 16/0072* (2013.01); *A61M 16/0075* (2013.01); *A61M 16/06* (2013.01); *A61M 16/0666* (2013.01); *A61M 16/109* (2014.02); *A61M 16/161* (2014.02); *A61M 16/204* (2014.02); *A61M 2016/0039* (2013.01); *A61M 2205/18* (2013.01); *A61M 2205/3368* (2013.01); *A61M 2205/3375* (2013.01); *A61M 2205/3389* (2013.01); *A61M 2205/3584* (2013.01); *A61M 2205/3592* (2013.01); *A61M 2205/368* (2013.01); *A61M 2205/3653* (2013.01); *A61M 2205/50* (2013.01); *A61M 2205/505* (2013.01); *A61M 2205/582* (2013.01); *A61M 2205/587* (2013.01); *A61M 2230/42* (2013.01)

(58) Field of Classification Search
CPC .............. A61M 16/109; A61M 16/161; A61M 16/204; A61M 16/0072; A61M 16/0075; A61M 16/06; A61M 16/0666; A61M 2016/0039; A61M 2205/18; A61M 2205/3368; A61M 2205/3375; A61M 2205/3389; A61M 2205/3584; A61M 2205/3592; A61M 2205/3653; A61M 2205/368; A61M 2205/50; A61M 2205/505; A61M 2205/582; A61M 2205/587; A61M 2230/42
USPC .................................................. 128/203.14
See application file for complete search history.

(56) References Cited

U.S. PATENT DOCUMENTS

| | | |
|---|---|---|
| 2008/0216832 A1 | 9/2008 | Carter et al. |
| 2010/0132707 A1 | 6/2010 | Muller |
| 2011/0164002 A1 | 7/2011 | Hill et al. |
| 2011/0259333 A1 | 10/2011 | Sanchez et al. |
| 2011/0284004 A1 | 11/2011 | Silver et al. |
| 2012/0192867 A1 | 8/2012 | Lewis et al. |
| 2013/0312754 A1 | 11/2013 | Garde et al. |

FOREIGN PATENT DOCUMENTS

| | | |
|---|---|---|
| WO | 2005007273 A1 | 1/2005 |
| WO | 2012139159 A1 | 10/2012 |
| WO | 2013124755 A1 | 8/2013 |

OTHER PUBLICATIONS

Resmed S9 Autoset™ CPAP and H5i™ Humidifier, Downloaded From http://respicarelb.com/index.php?route=product/product&product_id=50, on Jan. 30, 2014, 2 Pages.

Eu Pap, Philps Respironics System One Remstar Suto CPAP System, Downloaded From http://www.eu-pap.co.uk/system-oneo-remstar-auto-cpap.html on 1/30/204, 4 Pages.

SYSTEM AND METHOD FOR ADJUSTING HUMIDIFICATION DURING PRESSURE SUPPORT THERAPY

CROSS-REFERENCE TO PRIOR APPLICATIONS

This application is the U.S. National Phase application under 35 U.S.C. § 371 of International Application No. PCT/IB2015/057189, filed on Sep. 18, 2015, which claims the benefit of U.S. Provisional Application No. 62/051,977, filed on Sep. 18, 2014. These applications are hereby incorporated by reference herein.

BACKGROUND OF THE INVENTION

1. Field of the Invention

The present disclosure pertains to a pressure support system configured to adjust humidity and/or temperature of a pressurized flow of breathable gas delivered to a subject.

2. Description of the Related Art

It is well known to treat sleep disordered breathing by applying a positive air pressure (PAP) to the patient's airway. This positive pressure effectively "splints" the airway, thereby maintaining an open passage to the lungs. In one type of PAP therapy, known as continuous positive air pressure (CPAP), the pressure of gas delivered to the patient is constant throughout the patient's breathing cycle. It is also known to provide a positive pressure therapy in which the pressure of gas delivered to the patient varies with the patient's breathing cycle, or varies with the patient's effort, to increase the comfort to the patient. This pressure support technique is referred to as bi-level pressure support, in which the inspiratory positive airway pressure (IPAP) delivered to the patient is higher than the expiratory positive airway pressure (EPAP).

Humidifiers are frequently provided with a PAP machine in order to humidify the air generated by the PAP machine. Within the humidifier, water is allowed to evaporate to produce vapor within a reservoir while breathing gas is passed over the surface of the water. Increased water vapor within the reservoir increases the capability to provide more humidity to the gas that is delivered to a user. In a heated passover type of humidifier, this increase in gas stream humidity is accompanied by an increase in the gas stream temperature. When the ambient temperature around the PAP machine is below the gas stream temperature, condensation can form on the inside of the patient breathing circuit.

Patients are often confused about how to adjust humidification to achieve comfort. As pressure support therapy methods and/or devices offer more adjustable controls this problem is increased. Typically, with prior art systems, patients have the option to adjust humidification settings to increase comfort during therapy, however they do not know what to adjust, and/or necessary adjustments are so complex that the patient is discouraged from doing so.

SUMMARY

Accordingly, one or more aspects of the present disclosure relate to a pressure support system configured to adjust humidity and/or temperature of a pressurized flow of breathable gas delivered to a subject. The pressure support system comprises a pressure generator, a humidifier, one or more sensors, one or more physical computer processors, and/or other components. The pressure generator is configured to generate a pressurized flow of breathable gas for delivery to an airway of the subject. The humidifier is configured to humidify the pressurized flow of breathable gas. The one or more sensors are configured to generate output signals conveying information related to one or more parameters of the pressurized flow of breathable gas. The user interface is configured to receive entry and/or selection of feedback information from the subject indicating a comfort level with the pressurized flow of breathable gas. The one or more physical computer processors are configured by computer readable instructions to: control the pressure generator and the humidifier to deliver the pressurized flow of breathable gas to the subject according to a predetermined therapy regime based on the output signals; receive feedback information entered and/or selected through the user interface; cause one or more of the pressure generator or the humidifier to make an automatic adjustment to the pressurized flow of breathable gas to enhance the comfort level of the subject, the automatic adjustment based on the feedback information and the output signals, the automatic adjustment including adjustment of one or more of the pressure generator or the humidifier; receive additional feedback information entered and/or selected through the user interface subsequent to the automatic adjustment; and prompt the subject to manually adjust one or more of the pressure generator, the humidifier, or the ambient environment based on the additional feedback information.

Yet another aspect of the present disclosure relates to a method for adjusting humidity and/or temperature of a pressurized flow of breathable gas delivered to a subject with a pressure support system. The pressure support system comprises a pressure generator, a humidifier, one or more sensors, a user interface, one or more physical computer processors, and/or other components. The method comprises generating, with the pressure generator, a pressurized flow of breathable gas for delivery to an airway of the subject; humidifying, with the humidifier, the pressurized flow of breathable gas; generating, with the one or more sensors, output signals conveying information related to one or more parameters of the pressurized flow of breathable gas; controlling, with the one or more physical computer processors, the pressure generator and the humidifier to deliver the pressurized flow of breathable gas to the subject according to a predetermined therapy regime based on the output signals; receiving, with the user interface and/or the one or more physical computer processors, feedback information entered and/or selected through the user interface; causing, with the one or more physical computer processors, one or more of the pressure generator or the humidifier to make an automatic adjustment to the pressurized flow of breathable gas to enhance the comfort level of the subject, the automatic adjustment based on the feedback information and the output signals, the automatic adjustment including adjustment of one or more of the pressure generator or the humidifier; receiving, with the user interface and/or the one or more physical computer processors, additional feedback information entered and/or selected through the user interface subsequent to the automatic adjustment; and prompting, with the one or more physical computer processors, the subject to manually adjust one or more of the pressure generator, the humidifier, or the ambient environment based on the additional feedback information.

Still another aspect of the present disclosure relates to a pressure support system configured to adjust humidity and/or temperature of a pressurized flow of breathable gas delivered to a subject. The pressure support system comprising means for generating a pressurized flow of breathable gas for delivery to an airway of the subject; means for humidifying the pressurized flow of breathable gas; means for generating output signals conveying information related to one or more parameters of the pressurized flow of breathable gas; means for receiving entry and/or selection of feedback information from the subject indicating a comfort level with the pressurized flow of breathable gas; means for controlling the means for generating the pressurized flow of breathable gas and the means for humidifying to deliver the pressurized flow of breathable gas to the subject according to a predetermined therapy regime based on the output signals; means for receiving feedback information entered and/or selected through the means for receiving entry and/or selection; means for causing one or more of the means for generating the pressurized flow of breathable gas or the means for humidifying to make an automatic adjustment to the pressurized flow of breathable gas to enhance the comfort level of the subject, the automatic adjustment based on the feedback information and the output signals, the automatic adjustment including adjustment of one or more of the means for generating the pressurized flow of breathable gas or the means for humidifying; means for receiving additional feedback information entered and/or selected through the means for receiving entry and/or selection subsequent to the automatic adjustment; and means for prompting the subject to manually adjust one or more of the means for generating the pressurized flow of breathable gas, the means for humidifying, or the ambient environment based on the additional feedback information.

These and other objects, features, and characteristics of the present disclosure, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the disclosure.

DETAILED DESCRIPTION OF EXEMPLARY EMBODIMENTS

Figure 1:
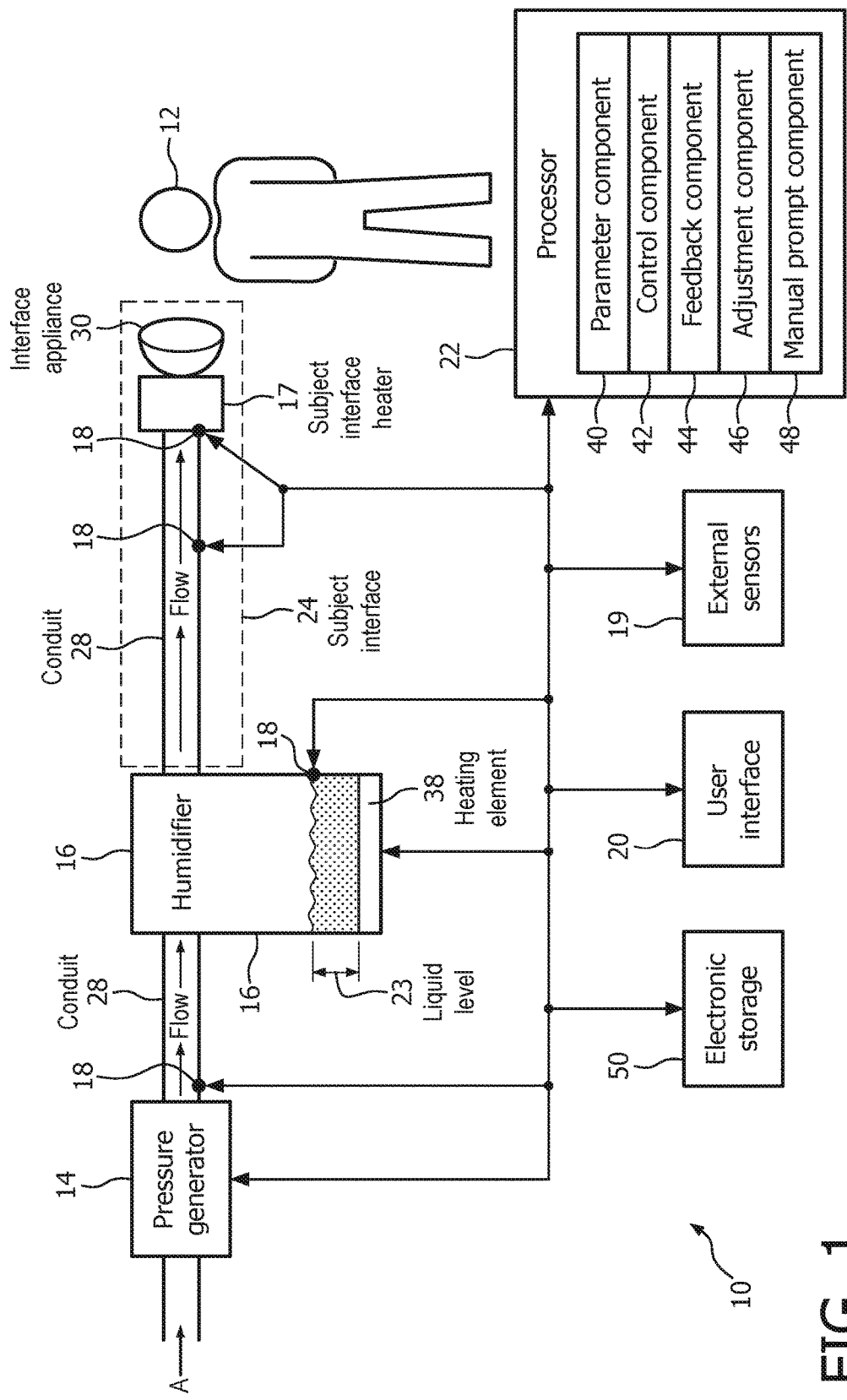
FIG. 1 illustrates a pressure support system configured to adjust humidity and/or temperature of a pressurized flow of breathable gas delivered to a subject.

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

FIG. 1 schematically illustrates a pressure support system 10 configured to adjust humidity and/or temperature of a pressurized flow of breathable gas delivered to a subject 12. In some embodiments, system 10 includes one or more of a pressure generator 14, a humidifier 16, a subject interface 24, a sensor 18, a user interface 20, a processor 22, electronic storage 50, and/or other components.

System 10 is configured to provide a humidity controlled pressurized flow of breathable gas to subject 12 according to a predetermined pressure support therapy regime. System 10 is configured to generate output signals and/or determine various parameters related to the pressurized flow of breathable gas. System 10 is configured to receive feedback from subject 12 related to a comfort level of subject 12 during therapy. System 10 is configured to automatically adjust the pressurized flow of breathable gas and/or the predetermined therapy regime, provide feedback to subject 12, and/or prompt subject 12 to make manual adjustments based on the output signals, the determined parameters, the feedback from subject 12, and/or other information. The feedback provided to subject 12 may include, for example, a recommendation to try a different therapy regime and/or alternate therapy devices, and/or other feedback. The manual adjustments may be, for example, manual adjustments to one or more components of system 10, manual adjustments to the ambient environment, and/or other manual adjustments. System 10 is configured to simplify adjustments to humidity control and/or pressure support therapy that enhance the comfort level of subject 12 during therapy.

For example, system 10 may determine, obtain, and/or receive information related to an ambient temperature, a relative ambient humidity, leak, the humidification method, humidification method set points (e.g., a target humidity level, etc.), a subject interface (e.g., conduit) temperature, water usage (e.g., per hour and/or per session), and/or other parameters. System 10 may receive feedback from subject 12 that includes information related to an inhaled air temperature rating (e.g., 0 being too cold, 10 being too hot), an inhaled air moisture rating (e.g., 0 is too dry, 10 is too wet), whether or not the subject 12 has experienced tube rainout, whether or not subject 12 has experienced mask rainout, and/or other information. System 10 is configured to analyze the parameter information and the feedback from subject 12 and make an automatic adjustment to the pressure support therapy regime, provide feedback to subject 12, prompt subject 12 and/or other users to make a manual adjustment to system 10 and/or the ambient environment, and/or take other actions. Other users may include a doctor, a caregiver, and/or other users. System 10 reduces the burden on subject 12 to determine which adjustments to make to increase his comfort level during therapy.

As illustrated in FIG. 1, pressure generator 14 is configured to generate a pressurized flow of breathable gas for delivery to an airway of subject 12. Pressure generator 14 may control one or more parameters of the flow of gas (e.g., flow rate, pressure, volume, temperature, gas composition, etc.) for therapeutic purposes, and/or for other purposes. By way of a non-limiting example, pressure generator 14 may be configured to control the flow rate and/or pressure of the flow of gas to provide pressure support to the airway of subject 12.

Pressure generator 14 receives a flow of gas from a gas source, such as the ambient atmosphere, as indicated by arrow A in FIG. 1 and elevates the pressure of that gas for delivery to the airway of a patient. Pressure generator 14 is any device, such as, for example, a pump, blower, piston, or bellows, that is capable of elevating the pressure of the received gas for delivery to subject 12. The present disclosure also contemplates that gas other than ambient atmospheric air may be introduced into system 10 for delivery to subject 12. In such embodiments, a pressurized canister or tank of gas containing air, oxygen, and/or another gas may supply the intake of pressure generator 14. In some embodiments, pressure generator 14 need not be provided, but instead the gas may be pressurized by the pressure of the canister and/or tank of pressurized gas itself.

In some embodiments, pressure generator 14 is a blower that is driven at a substantially constant speed during the course of the pressure support treatment to provide the pressurized flow of breathable gas with a substantially constant elevated pressure and/or flow rate. Pressure generator 14 may comprise a valve for controlling the pressure/flow of gas. The present disclosure also contemplates controlling the operating speed of the blower, either alone or in combination with such a valve, to control the pressure/flow of gas provided to the patient.

Humidifier 16 is configured to humidify the pressurized flow of breathable gas. Humidifier 16 may comprise a humidification chamber, a gas inlet, a gas outlet, a heating element 38, and/or other components. In some embodiments, humidifier 16 is a warm mist humidifier (e.g., a vaporizer) configured to generate water vapor by heating liquid held within humidifier 16 via heating element 38. Humidifier 16 may comprise an inductive heater configured to heat the liquid held within humidifier 16 via inductive heating. Humidifier 16 is configured such that the flow of gas is received from pressure generator 14 by humidifier 16 through a gas inlet and is humidified within a humidification chamber by the water vapor before being released from the humidification chamber through a gas outlet. The gas outlet of the humidifier is coupled with subject interface 24 such that the humidified flow of gas is delivered to the airway of subject 12 through subject interface 24.

Heating element 38 is configured to controllably elevate the temperature of liquid within the humidification chamber. In some embodiments, heating element 38 is positioned at the bottom of the humidification chamber in proximity to liquid in the humidification chamber. The heat emitted by heating element 38 is dispensed directly into the liquid in the humidification chamber. This emission of heat by heating element 38 into the liquid vaporizes the liquid.

The pressurized flow of breathable gas is delivered to the airway of subject 12 from pressure generator 14 and/or humidifier 16 via subject interface 24. Subject interface 24 is configured to communicate the pressurized flow of breathable gas generated by pressure generator 14 and/or humidified by humidifier 16 to the airway of subject 12. As such, subject interface 24 comprises one or more conduits 28, an interface appliance 30, a subject interface heater 17, and/or other components. Conduits 28 are configured to convey the pressurized flow of gas to interface appliance 30. Interface appliance 30 is configured to deliver the flow of gas to the airway of subject 12. In some embodiments, interface appliance 30 is non-invasive. As such, interface appliance 30 non-invasively engages subject 12. Non-invasive engagement comprises removably engaging an area (or areas) surrounding one or more external orifices of the airway of subject 12 (e.g., nostrils and/or mouth) to communicate gas between the airway of subject 12 and interface appliance 30. Some examples of non-invasive interface appliance 30 may comprise, for example, a nasal cannula, a nasal mask, a nasal/oral mask, a full face mask, a total face mask, or other interface appliances that communicate a flow of gas with an airway of a subject. The present disclosure is not limited to these examples, and contemplates delivery of the flow of gas to the subject using any interface appliance.

Although subject interface 24 is illustrated in FIG. 1 as a single-limbed circuit for the delivery of the flow of gas to the airway of subject 12, this is not intended to be limiting. The scope of this disclosure comprises double-limbed circuits having a first limb configured to both provide the flow of gas to the airway of the subject, and a second limb configured to selectively exhaust gas from subject interface 24 (e.g., to exhaust exhaled gases).

Subject interface heater 17 is configured to controllably heat the pressurized flow of breathable gas in subject interface 24. Subject interface heater 17 is illustrated in FIG. 1 at a single location within (or in communication with) conduit 28 near interface appliance 30, and/or within interface appliance 30. The illustrated position of subject interface heater 17 is not intended to be limiting. Subject interface heater 17 may be located in any position that allows it to controllably heat the pressurized flow of breathable gas in subject interface 24. Subject interface heater 17 may be configured to heat the pressurized flow of breathable gas continuously along the entire length of conduit 28, for example. Subject interface heater 17 may be configured to heat the pressurized flow of breathable gas by dissipating electrical current (e.g., resistive heating), and/or by other methods. Subject interface heater 17 may comprise one or more of a heating coil, a heating jacket, heating tape, and/or other heating devices. Subject interface heater 17 may be configured to heat the gas in subject interface 24 directly and/or indirectly. In some embodiments, a heating coil may be positioned within conduit 28 in fluid communication with the pressurized flow of breathable gas to directly heat the gas flow. In some embodiments, a heating jacket may be placed around conduit 28 to heat the flow of gas indirectly by transferring heat through the wall of conduit 28.

Sensor 18 is configured to generate output signals conveying information related to one or more parameters of the pressurized flow of breathable gas. Information related to one or more parameters of the pressurized flow of breathable gas may include information related to a flow rate, a volume, a pressure, humidity, temperature, acceleration, velocity, and/or other gas parameters; breathing parameters related to the respiration of subject 12 such as a tidal volume, a timing (e.g., beginning and/or end of inhalation, beginning and/or end of exhalation, etc.), a respiration rate, a duration (e.g., of inhalation, of exhalation, of a single breathing cycle, etc.), respiration frequency, and/or other breathing parameters; parameters related to the operation of pressure generator 14, humidifier 16, subject interface heater 17, and/or other components of system 10; parameters related to the ambient environment, and/or other information. Sensor 18 may comprise one or more sensors that measure such parameters directly (e.g., through communication with the pressurized flow of breathable gas in conduit 28). Sensor 18 may comprise one or more sensors that generate output signals related to the pressurized flow of breathable gas indirectly. For example, sensor 18 may comprise one or more sensors configured to generate an output based on an operating parameter of pressure generator 14, humidifier 16, and/or subject interface heater 17 (e.g., a current drawn, voltage, and/or other operating parameters), and/or other sensors.

Sensor 18 may include pressure sensors, flow rate sensors, volume sensors, humidity sensors, liquid level sensors, usage time sensors, temperature sensors, external sensors 19, and/or other sensors. External sensors 19 may include, for example, altitude sensors, home heating/cooling mode/settings sensors (e.g., configured to generate output signals conveying information related to home HVAC mode, settings, mode cycle, etc.), room ambient conditions sensors, home exterior ambient conditions sensors, and/or other sensors. Sensors 18 and/or 19 may include a plurality of individual sensors located at various locations throughout system 10, in the immediate sleeping area, in the home and/or positioned to generate information about conditions exterior to the home (e.g., environmental conditions measured by the system and/or retrieved from some other system or database). FIG. 1 illustrates four different locations for individual sensors 18 and one location of external sensors 19. This is not intended to be limiting. System 10 may include any number of sensors 18 and/or 19 located anywhere within system 10 and/or in proximity to system 10 provided system 10 functions as described herein. For example, sensor 18 may include one or more pressure, flow rate, humidity, temperature, and/or other sensors in communication with the pressurized flow of breathable gas in conduit 28. Sensor 18 may be and/or include a transducer configured to detect acoustic waves transmitted through subject interface 24. These acoustic waves may convey information related to respiratory effort of the subject, and/or the noise generated by the subject during respiration (e.g., during snoring). Sensor 18 may be and/or include liquid level sensors configured to generate one or more output signals conveying information related to a current liquid level 23 in humidifier 16. In this example, sensor 18 may be and/or include one or more of a float switch, a pressure sensor, an ultrasonic sensor, a heat capacity based sensor, and/or other liquid level sensors. Sensor 18 may be and/or include usage time sensors configured to generate one or more output signals conveying information related to one or more usage time parameters. The one or more usage time parameters may comprise parameters related to the total time subject 12 spends connected to system 10 during a usage session, and/or time subject 12 is asleep while connected to system 10 during a usage session. Sensor 18 may include one or more subject interface temperature sensors configured to generate one or more output signals conveying information related to the temperature of one or more components of subject interface 24. Sensor 18 may include one or more environmental sensors configured to generate output signals related to conditions (e.g., temperature, humidity) of the ambient environment around system 10.

User interface 20 is configured to receive entry and/or selection of feedback information from subject 12 and/or other users indicating an initial comfort level with the pressurized flow of breathable gas. After an automatic adjustment to the pressurized flow of breathable gas (described below) user interface 20 is configured to receive entry and/or selection of additional feedback information from the subject indicating an adjusted comfort level. User interface 20 is configured to provide an interface between system 10 and subject 12 and/or other users (e.g., a doctor, care-giver, etc.) through which subject 12 may provide information to and receive information from system 10. This enables data, cues, results, and/or instructions and any other communicable items, collectively referred to as "information," to be communicated between subject 12 and one or more of pressure generator 14, electronic storage 50, processor 22, and/or other components of system 10. Examples of interface devices suitable for inclusion in user interface 20 comprise a keypad, buttons, switches, a keyboard, knobs, levers, a display screen, a touch screen, speakers, a microphone, an indicator light, an audible alarm, a printer, a tactile feedback device, and/or other interface devices.

It is to be understood that other communication techniques, either hard-wired or wireless, are also contemplated by the present disclosure as user interface 20. For example, the present disclosure contemplates that user interface 20 may be integrated with a removable storage interface provided by electronic storage 50. In this example, information may be loaded into system 10 from removable storage (e.g., a smart card, a flash drive, a removable disk, etc.) that enables the user(s) to customize the implementation of system 10. Other exemplary input devices and techniques adapted for use with system 10 as user interface 20 comprise, but are not limited to, an RS-232 port, RF link, an IR link, modem (telephone, cable or other). In short, any technique for communicating information with system 10 is contemplated by the present disclosure as user interface 20.

In some embodiments, user interface 20 comprises a plurality of separate interfaces. In some embodiments, user interface 20 comprises at least one interface that is provided integrally with pressure generator 14. In some embodiments, user interface 20 includes one or more of a user interface that is integral with pressure generator 14 and/or a graphical user interface presented to subject 12 via a client computing device (not shown in FIG. 1). For example, user interface 20 may be and/or include a graphical user interface that is presented to subject 12 on a smartphone and/or other computing device associated with subject 12. This may allow subject 12 to provide feedback to system 10, receive feedback from system 10, and/or receive a prompt to make a manual adjustment (for example) during therapy and/or at other times while subject 12 is not in immediate proximity to pressure generator 14 and/or humidifier 16, for example.

Processor 22 is configured to provide information processing capabilities in system 10. As such, processor 22 may comprise one or more of a digital processor, an analog processor, a digital circuit designed to process information, an analog circuit designed to process information, a state machine, and/or other mechanisms for electronically processing information. Although processor 22 is shown in FIG. 1 as a single entity, this is for illustrative purposes only. In some embodiments, processor 22 may comprise a plurality of processing units. These processing units may be physically located within the same device (e.g., pressure generator 14, humidifier 16, a client computing device), or processor 22 may represent processing functionality of a plurality of devices operating in coordination.

As shown in FIG. 1, processor 22 is configured to execute one or more computer program components. The one or more computer program components may include one or more of a parameter component 40, a control component 42, a feedback component 44, an adjustment component 46, a manual prompt component 48, and/or other components. Processor 22 may be configured to execute components 40, 42, 44, 46, and/or 48 by software; hardware; firmware; some combination of software, hardware, and/or firmware; and/or other mechanisms for configuring processing capabilities on processor 22.

It should be appreciated that although components 40, 42, 44, 46, and 48 are illustrated in FIG. 1 as being co-located within a single processing unit, in embodiments in which processor 22 includes multiple processing units, one or more of components 40, 42, 44, 46, and/or 48 may be located remotely from the other components. The description of the functionality provided by the different components 40, 42, 44, 46, and/or 48 described below is for illustrative purposes, and is not intended to be limiting, as any of components 40, 42, 44, 46, and/or 48 may provide more or less functionality than is described. For example, one or more of components 40, 42, 44, 46, and/or 48 may be eliminated, and some or all of its functionality may be provided by other components 40, 42, 44, 46, and/or 48. As another example, processor 22 may be configured to execute one or more additional components that may perform some or all of the functionality attributed below to one of components 40, 42, 44, 46, and/or 48.

Parameter component 40 is configured to determine one or more parameters related to the pressurized flow of breathable gas. Parameter component 40 is configured to determine the one or more parameters based on the output signals from sensor 18 and/or other information. The one or more parameters related to the pressurized flow of breathable gas may comprise, for example, one or more of a flow rate, a volume, a pressure, humidity of the gas, temperature of the gas, acceleration, velocity, ambient temperature, a relative ambient humidity, leak, the humidification method, humidification method set points (e.g., a target humidity level, heater plate temperature, etc.), a subject interface (e.g., conduit) temperature, water usage (e.g., per hour and/or per session), altitude, home heating/cooling mode/settings, and/or other parameters. In some embodiments, parameter component 40 is configured to obtain operational status indicators generated by pressure generator 14 and/or humidifier 16, for example, that indicate an operational status of the individual component. The operational status indicators may indicate, for example, whether individual devices within a given component are operating as expected, for example (e.g., heating element 38 of humidifier 16 provides heat when required). The information determined by parameter component 40 may be used to control system 10 according to a predetermined therapy regime, adjust the therapy provided to subject 12, determine whether to prompt subject 12 and/or other users to manually adjust one or more components of system 10, and/or for other uses.

Control component 42 is configured to control pressure generator 14, humidifier 16, subject interface 24 (e.g., subject interface heater 17), and/or other components to deliver the pressurized flow of breathable gas to subject 12. Control component 42 is configured to control pressure generator 14, humidifier 16, subject interface 24, and/or other components according to a predetermined therapy regime. Control component 42 is configured to control pressure generator 14, humidifier 16, subject interface 24, and/or other components based on the output signals from sensor 18, information determined by parameter component 40, and/or other information. By way of non-limiting example, processor 22 may control pressure generator 14 such that the pressure support provided to the subject via the flow of gas comprises, non-invasive ventilation, positive airway pressure support, continuous positive airway pressure support, bi-level support, BiPAP®, and/or other types of pressure support therapy.

In some embodiments, control component 42 is configured such that the predetermined therapy regime is based on typical ambient weather conditions during a given season of the year, previous feedback information from the subject received during the given season, information from a thermostat controlling the temperature of the environment where pressure support therapy occurs, and/or other information. Control component 42 may be configured to wirelessly (and/or via wires) communicate with external resources via a network (e.g., the internet) to obtain such information. For example, control component 42 may determine the season of the year based on information retrieved from an external server that stores information related to the ambient weather. Control component 42 may obtain previous feedback information from the subject that is stored in electronic storage 50, for example, and/or in other locations. The information may be stored in electronic storage 50 with identifiers that convey when (e.g., the date) the information was received and/or stored, for example. Control component 42 may retrieve information from the thermostat controlling the temperature of the environment via a local area network and/or other networks, for example.

Feedback component 44 is configured to receive feedback information entered and/or selected through user interface 20. Feedback component 44 is configured to receive entry and/or selection of feedback information from subject 12 indicating an initial comfort level with the pressurized flow of breathable gas. After an automatic adjustment to the pressurized flow of breathable gas (described below) feedback component 44 is configured to receive entry and/or selection of additional feedback information from the subject indicating an adjusted comfort level. In some embodiments, feedback component 44 is configured to control user interface 20 to present one or more views of a graphical user interface to subject 12 that facilitate entry and/or selection of the feedback information. In some embodiments, the feedback information includes information related to an inhaled air temperature, an inhaled air moisture, whether or not the subject 12 has experienced tube rainout, whether or not subject 12 has experienced mask rainout, and/or other information.

In some embodiments, feedback component 44 may be configured such that the one or more views of the graphical user interface presented to subject 12 via user interface 20 facilitate rating at least some portions of the feedback information according to a predetermined ratings scale. For example, feedback component 44 may facilitate rating the inhaled air temperature (e.g., 0 being too cold, 10 being too hot), rating the inhaled air moisture (e.g., 0 is too dry, 10 is too wet), and/or rating other factors.

Adjustment component 46 is configured to make an automatic adjustment to the pressurized flow of breathable gas to enhance the comfort level of subject 12. The automatic adjustment may be made based on the received feedback information (e.g., via feedback component 44), the output signals from sensor 18, the information determined by parameter component 40, and/or other information. The automatic adjustment may include adjustment of pressure generator 14, humidifier 16, subject interface 24, and/or other components of system 10.

In some embodiments, as described above, user interface 20 and/or feedback component 44 is configured to receive additional feedback information entered and/or selected through user interface 20 subsequent to an automatic adjustment made by adjustment component 46. In some embodiments, adjustment component 46 is configured to make an additional automatic adjustment to the pressurized flow of breathable gas to enhance the comfort level of subject 12. The additional automatic adjustment may be made based on the additional feedback information, the output signals from sensor 18, the information determined by parameter component 40, and/or other information. The additional automatic adjustment may include adjustment of pressure generator 14, humidifier 16, subject interface 24, and/or other components of system 10. In some embodiments, adjustment component 46 is configured such that the adjustment, feedback, adjustment process is repeated (e.g., iterated) one or more times. Adjustment component 46 may be configured to repeat the adjustment and feedback cycle when the feedback information indicates that the comfort level of subject 12 is improving, for example. In some embodiments, adjustment component 46 is configured to cease automatic adjustments responsive to the feedback information indicating that subject 12 is comfortable, the feedback information indicating that the comfort level of subject 12 is not improving (e.g., the temperature of the inhaled air is still too cold for subject 12, rainout still occurs even after all of the automatic adjustments, etc.), and/or for other reasons.

Manual prompt component 48 is configured to determine whether to prompt subject 12 and/or other users to make a manual adjustment to system 10 and/or external factors associated with system 10. Manual prompt component 48 may be configured to control user interface 20 to prompt subject 12 and/or other users. The manual adjustment may include, for example, manual adjustments to one or more components of system 10, manual adjustments to the ambient environment, manually adjusting the therapy location, and/or other manual adjustments. A manual adjustment may include an adjustment to pressure generator 14, humidifier 16, subject interface 24, and/or other components of system 10. In some embodiments, the prompted manual adjustment includes changing the temperature of the ambient environment, changing a type of therapy of the predetermined therapy regime, changing physical components of the pressure support system (e.g., adding and/or removing a heater for conduit 28 (e.g., subject interface heater 17), changing the tank capacity of humidifier 16, changing a mask (e.g., interface appliance 30) that has excessive leak), and/or other manual adjustments. In some embodiments, the manual adjustments include manually changing therapy set points (e.g., target humidity level, target temperature, etc.) via user interface 20, for example. Manual prompt component 48 is configured to determine whether to prompt subject 12 and/or other users based on the additional feedback information subsequent to the automatic adjustment, the output signals from sensor 18, the information determined by parameter component 40, the automatic adjustments to the pressurized flow of breathable gas, and/or other information.

In some embodiments, manual prompt component 48 is configured such that subject 12 and/or other users are prompted to make a manual adjustment only if necessary. Subject 12 and/or other users may be prompted to make a manual adjustment if the automatic adjustment to the pressurized flow of breathable, for example, gas does not enhance the comfort level of subject 12, does not enhance the comfort level by a predetermined amount, and/or for other reasons. For example, manual prompt component 48 may be configured to prompt subject 12 to try a different pressure generator, humidifier, and/or subject interface (e.g., prompt a switch from a subject interface that does not include a heater to one that does include a heater), and/or run a system diagnostic if the present components of system 10 are unable to be adjusted enough to satisfy the needs of subject 12.

The description of an automatic adjustment by adjustment component 46 and then, if necessary, a prompted manual adjustment is not intended to be limiting. In some embodiments, manual prompt component 48 is configured to prompt subject 12 and/or other users to make a manual adjustment before any automatic adjustment by adjustment component 46. In these embodiments, adjustment component 46 may not make an automatic adjustment at all and/or make an automatic adjustment only after manual prompt component 48 prompts a manual adjustment.

In some embodiments, manual prompt component 48 is configured to provide feedback to subject 12 via user interface 20 and/or other components of system 10. For example, manual prompt component 48 may be configured to notify subject 12 if parameter component 40 obtains operational status indicators that indicate, for example, that individual devices within a given component are not operating as expected (e.g., heating element 38 of humidifier 16 does not provide heat when required, a heating element of subject interface heater 17 does not provide heat when required, sensor 18 is out of range, expected leak is out of range, environmental conditions exceed system capabilities, pressure generator 14 malfunctions and/or feedback components are unavailable.)

Figure 2:
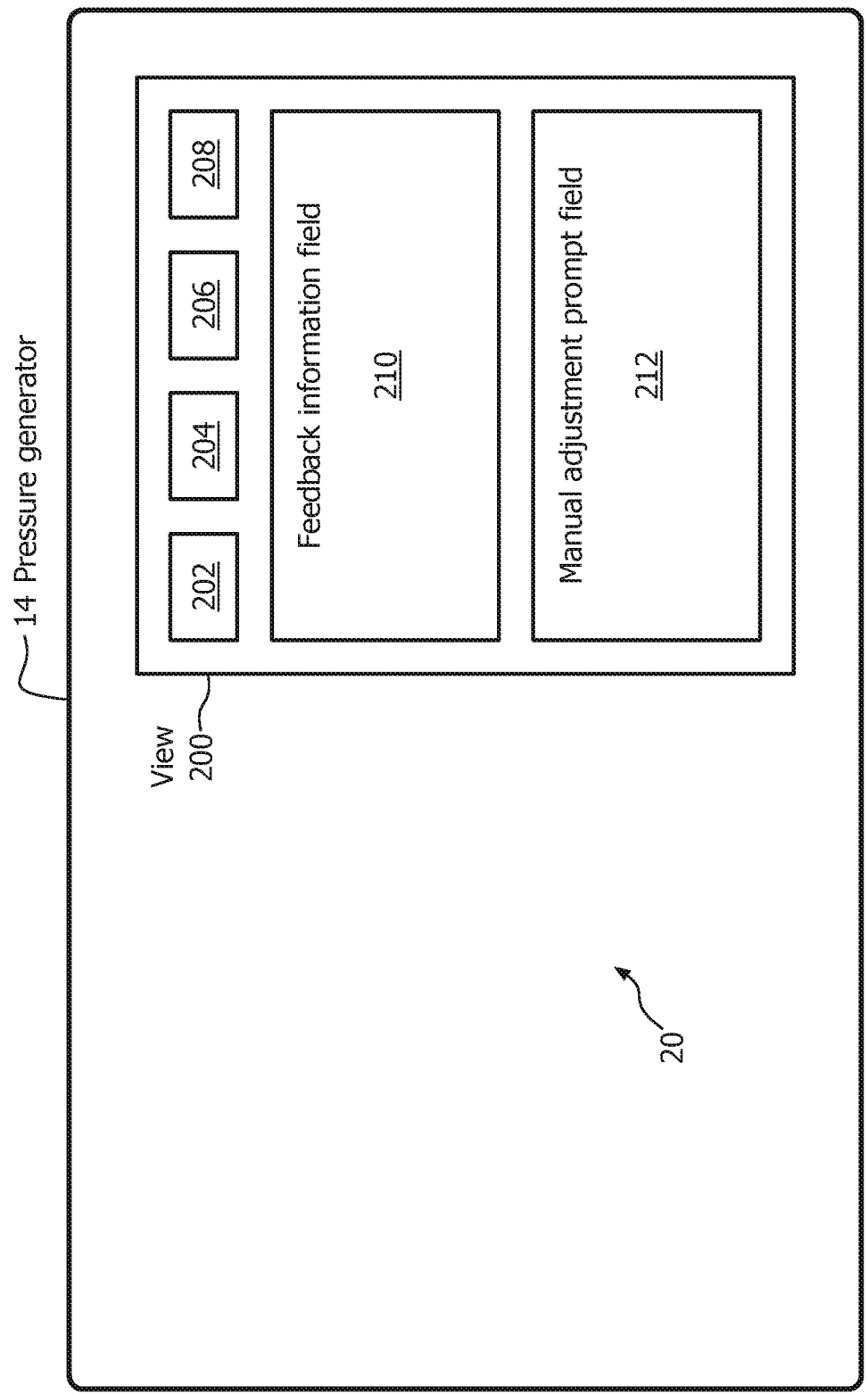
FIG. 2 illustrates a view of a graphical user interface presented to the subject.

By way of a non-liming example, FIG. 2 illustrates of a view 200 of user interface 20 presented to subject 12 (FIG. 1) and/or other users. In FIG. 2, user interface 20 is integral with pressure generator 14. View 200 includes parameter fields 202, 204, 206, and 208, a feedback information field 210, and a manual adjustment prompt field 212. One or more components of processor 22 may control user interface 20 (as described above) to provide information to and/or receive information from subject 12 and/or other users. For example, one or more parameters determined by parameter component 40 may be displayed to subject 12 via parameter fields 202-208. Parameters such as ambient temperature, ambient relative humidity, the type of pressure support therapy and/or humidification, pressure support therapy and/or humidification set points, leak, an operational status indicator (e.g., indicating whether components of system 10 are operating normally), and/or other parameters.

Feedback information field 210 is configured to receive entry and/or selection of feedback information from subject 12 and/or other users. Field 210 may be touch sensitive (e.g., a touchscreen) so that subject 12 and/or the other users may enter information by touching field 210. Field 210 may display information entered via a keyboard, keypad, and/or other entry device.

Manual adjustment prompt field 212 may be configured to display prompts to the user to facilitate adjustment of system 10, make recommendations to subject 12, and/or provide other information. For example, field 212 may display messages such as, "Increase the room temperature," and/or, "Change to a subject interface that includes a heated tube," and/or other informational messages. Recommendations may be related to, for example, the pressure support therapy and/or humidification method, pressure support therapy and/or humidification method set points, and/or other information.

Figure 3:
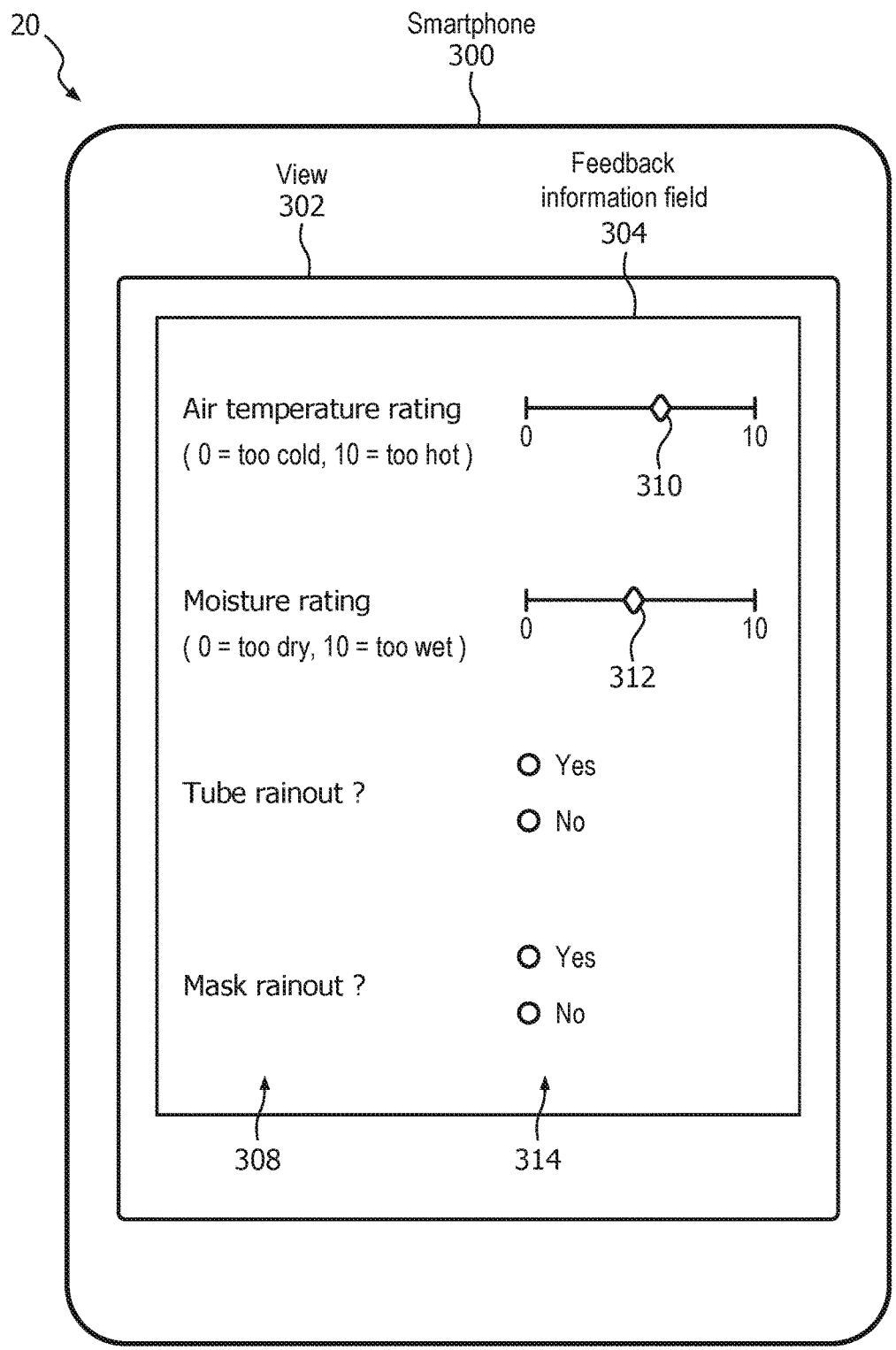
FIG. 3 illustrates a second view of the graphical user interface.

By way of a second non-limiting example, FIG. 3 illustrates a view 302 of user interface 20 presented to subject 12 (FIG. 1) and/or other users via a display of a smartphone 300 and/or other mobile computing device associated with subject 12. View 302 includes feedback information field 304. In the example shown in FIG. 3, feedback component 44 (FIG. 1) has controlled field 304 to display survey questions 308. The survey questions are configured to facilitate entry and/or selection of information related to the comfort level of subject 12 during therapy. In the example shown in FIG. 3, subject 12 may provide information by dragging and dropping an indicator 310, 312 on a scale of 1 to 10, and/or activating YES/NO indicators 314. These options are not intended to be limiting. Feedback component 44 may control field 304 to facilitate entry and/or selection of comfort level information in any way that allows system 10 to operate as described herein.

Returning to FIG. 1, electronic storage 50 comprises electronic storage media that electronically stores information. The electronic storage media of electronic storage 50 may comprise one or both of system storage that is provided integrally (i.e., substantially non-removable) with system 10 and/or removable storage that is removably connectable to system 10 via, for example, a port (e.g., a USB port, a firewire port, etc.) or a drive (e.g., a disk drive, etc.). Electronic storage 50 may comprise one or more of optically readable storage media (e.g., optical disks, etc.), magnetically readable storage media (e.g., magnetic tape, magnetic hard drive, floppy drive, etc.), electrical charge-based storage media (e.g., EEPROM, RAM, etc.), solid-state storage media (e.g., flash drive, etc.), and/or other electronically readable storage media. Electronic storage 50 may store software algorithms, information determined by processor 22, information received via user interface 20, and/or other information that enables system 10 to function properly. Electronic storage 50 may be (in whole or in part) a separate component within system 10, or electronic storage 50 may be provided (in whole or in part) integrally with one or more other components of system 10 (e.g., user interface 20, pressure generator 14, processor 22, etc.).

By way of a non-limiting example, electronic storage 50 may be configured to store information related to a comfort level of subject 12 and corresponding parameters of the pressurized flow of breathable gas. Electronic storage 50 may be configured to store information related to ambient weather conditions, a season of the year, and/or other information that corresponds to the comfort level of subject 12, parameters of the pressurized flow of breathable gas, and/or other information.

Figure 4:
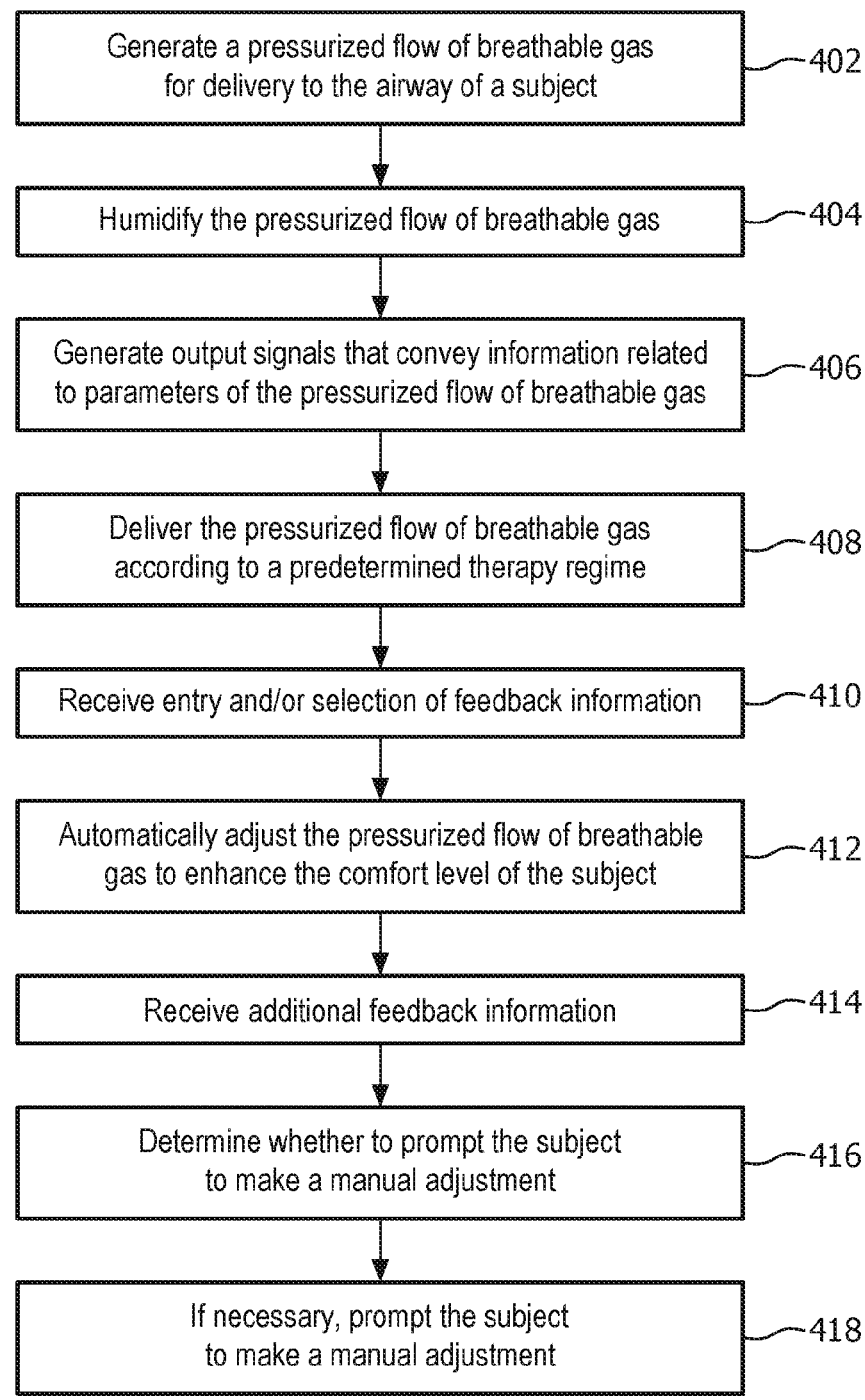
FIG. 4 illustrates a method for adjusting humidity of a pressurized flow of breathable gas delivered to the airway of a subject with a pressure support system.

FIG. 4 illustrates a method 400 for adjusting humidity of a pressurized flow of breathable gas delivered to the airway of a subject with a pressure support system. The pressure support system comprises a pressure generator, a humidifier, one or more sensors, a user interface, one or more physical computer processors, a subject interface, and/or other components. The operations of method 400 presented below are intended to be illustrative. In some embodiments, method 400 may be accomplished with one or more additional operations not described, and/or without one or more of the operations discussed. Additionally, the order in which the operations of method 400 are illustrated in FIG. 4 and described below is not intended to be limiting.

In some embodiments, method 400 may be implemented in one or more processing devices (e.g., a digital processor, an analog processor, a digital circuit designed to process information, an analog circuit designed to process information, a state machine, and/or other mechanisms for electronically processing information). The one or more processing devices may include one or more devices executing some or all of the operations of method 400 in response to instructions stored electronically on an electronic storage medium. The one or more processing devices may include one or more devices configured through hardware, firmware, and/or software to be specifically designed for execution of one or more of the operations of method 400.

At an operation 402, a pressure generator generates a pressurized flow of breathable gas for delivery to the airway of the subject. In some embodiments, operation 402 is performed by a pressure generator the same as or similar to pressure generator 14 (shown in FIG. 1 and described herein).

At an operation 404, the pressurized flow of breathable gas is humidified. In some embodiments, operation 404 is performed by a humidifier the same as or similar to humidifier 16 (shown in FIG. 1 and described herein).

At an operation 406, output signals that convey information related to one or more parameters of the pressurized flow of breathable gas are generated. In some embodiments, operation 406 is performed by one or more sensors the same as or similar to sensor 18 (shown in FIG. 1 and described herein).

At an operation 408, the pressurized flow of breathable gas is delivered to the subject according to a predetermined therapy regime. The pressure generator, the humidifier, the subject interface (e.g., a subject interface heater of the subject interface), and/or other components of the system may be controlled by the one or more processors to deliver the pressurized flow of breathable gas according to the predetermined therapy regime. The one or more processors may control the pressure generator, the humidifier, the subject interface, the subject interface heater, and/or the other components based on the output signals. In some embodiments, the predetermined therapy regime is based on typical ambient weather conditions during a given season of the year and previous feedback information from the subject received during the given season. In some embodiments, operation 408 is performed by one or more physical computer processors, a pressure generator, a humidifier, a subject interface, and a subject interface heater the same as or similar to processor 22, pressure generator 14, humidifier 16, subject interface 24, and subject interface heater 17 (shown in FIG. 1 and described herein).

At an operation 410, entry and/or selection of feedback information is received from the subject. The feedback information indicates a comfort level of the subject with the pressurized flow of breathable gas. In some embodiments, operation 410 is performed by a user interface and/or one or more physical computer processors the same as or similar to user interface 20 and/or processor 22 (shown in FIG. 1 and described herein). In some embodiments, the user interface includes one or more of a user interface that is integral with the pressure generator or a graphical user interface presented to the subject via a mobile computing device.

At an operation 412, the pressurized flow of breathable gas is automatically adjusted. The pressurized flow of breathable gas is automatically adjusted to enhance the comfort level of the subject. One or more of the pressure generator, the humidifier, the subject interface (e.g., the subject interface heater), and/or the other components are caused to make the automatic adjustment by the one or more physical computer processors. The automatic adjustment is based on the received feedback information, the output signals, and/or other information. In some embodiments, operation 412 is performed by one or more physical computer processors the same as or similar to processor 22 (shown in FIG. 1 and described herein).

At an operation 414, additional feedback information is received. The additional feedback information may be entered by and/or received from a subject subsequent to the automatic adjustment. In some embodiments, operation 414 is performed by one or more physical computer processors and/or a user interface the same as or similar to processor 22 and/or user interface 20 (shown in FIG. 1 and described herein).

At an operation 416, a determination of whether or not to prompt the subject to make a manual adjustment of the pressure generator, the humidifier, the subject interface, the ambient environment, and/or other components/factors is made. The determination of whether to prompt the manual adjustment is made based on the additional feedback information, the output signals, the automatic adjustment to the pressurized flow of breathable gas, and/or other information. In some embodiments, operation 416 is performed by one or more physical computer processors the same as or similar to processor 22 (shown in FIG. 1 and described herein).

At an operation 418, if necessary, the user is prompted to make a manual adjustment. The user is prompted to make a manual adjustment if the automatic adjustment to the pressurized flow of breathable gas does not enhance the comfort level of the subject and/or does not enhance the comfort level by a predetermined amount, and/or for other reasons. The prompted manual adjustment may include changing the temperature of the ambient environment, changing a type of therapy of the predetermined therapy regime, changing physical components of the pressure support system, and/or other manual adjustments. In some embodiments, operation 418 is performed by a pressure generator the same as or similar to pressure generator 14 (shown in FIG. 1 and described herein).

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the description provided above provides detail for the purpose of illustration based on what is currently considered to be the most practical and preferred embodiments, it is to be understood that such detail is solely for that purpose and that the disclosure is not limited to the expressly disclosed embodiments, but, on the contrary, is intended to cover modifications and equivalent arrangements that are within the spirit and scope of the appended claims. For example, it is to be understood that the present disclosure contemplates that, to the extent possible, one or more features of any embodiment can be combined with one or more features of any other embodiment.

What is claimed is:

1. A pressure support system configured to adjust humidity and/or temperature of a pressurized flow of breathable gas delivered to a subject, the pressure support system comprising:
   a pressure generator configured to generate a pressurized flow of breathable gas for delivery to an airway of the subject;
   a humidifier configured to humidify the pressurized flow of breathable gas;
   one or more sensors configured to generate output signals conveying information related to one or more parameters of the pressurized flow of breathable gas;
   a user interface configured to receive entry and/or selection of feedback information from the subject indicating a comfort level with the pressurized flow of breathable gas; and
   one or more physical computer processors configured by computer readable instructions to:
      control the pressure generator and the humidifier to deliver the pressurized flow of breathable gas to the subject according to a predetermined therapy regime based on the output signals;
      receive feedback information entered and/or selected through the user interface;
      make an automatic adjustment to the pressurized flow of breathable gas to enhance the comfort level of the subject, the automatic adjustment based on the received feedback information and the output signals, the automatic adjustment including adjustment of one or more of the pressure generator or the humidifier;
      receive additional feedback information entered and/or selected through the user interface subsequent to the automatic adjustment; and
      prompt the subject to manually adjust one or more of the pressure generator, the humidifier, or an ambient environment based on the additional feedback information.

2. The system of claim 1, further comprising a subject interface configured to deliver the pressurized flow of breathable gas to the airway of the subject,
   wherein the one or more physical computer processors are further configured to control the subject interface, the pressure generator, and the humidifier to deliver the pressurized flow of breathable gas to the subject according to the predetermined therapy regime based on the output signals,
   wherein the automatic adjustment includes adjustment of one or more of the pressure generator, the humidifier, or the subject interface; and
   wherein the one or more physical computer processors are further configured to prompt the subject to manually adjust the subject interface based on the additional feedback information.

3. The system of claim 1, further comprising a subject interface configured to deliver the pressurized flow of breathable gas to the airway of the subject that includes a subject interface heater configured to controllably heat the pressurized flow of breathable gas in the subject interface,
   wherein the one or more physical computer processors are further configured to control the subject interface heater, the pressure generator, and the humidifier to deliver the pressurized flow of breathable gas to the subject according to the predetermined therapy regime based on the output signals,
   wherein the automatic adjustment includes adjustment of one or more of the pressure generator, the humidifier, or the subject interface heater; and
   wherein the one or more physical computer processors are further configured to prompt the subject to manually adjust the subject interface based on the additional feedback information.

4. The system of claim 1, wherein the one or more physical computer processors are configured such that a prompted manual adjustment includes one or more of changing the temperature of the ambient environment, changing a type of therapy of the predetermined therapy regime, or changing physical components of the pressure support system.

5. The system of claim 1, wherein in the user interface includes one or more of a user interface that is integral with the pressure generator or a graphical user interface presented to the subject via a mobile computing device.

6. The system of claim 1, wherein the one or more physical computer processors are configured such that the predetermined therapy regime is based on typical ambient weather conditions during a given season of the year and/or previous feedback information from the subject received during the given season.

7. A method for adjusting humidity and/or temperature of a pressurized flow of breathable gas delivered to a subject with a pressure support system, the pressure support system comprising a pressure generator, a humidifier, one or more sensors, a user interface, and one or more physical computer processors, the method comprising:
   generating, with the pressure generator, a pressurized flow of breathable gas for delivery to an airway of the subject;
   humidifying, with the humidifier, the pressurized flow of breathable gas;
   generating, with the one or more sensors, output signals conveying information related to one or more parameters of the pressurized flow of breathable gas;
   controlling, with the one or more physical computer processors, the pressure generator and the humidifier to deliver the pressurized flow of breathable gas to the subject according to a predetermined therapy regime based on the output signals;
   receiving, with the user interface, entry and/or selection of feedback information from the subject indicating a comfort level with the pressurized flow of breathable gas;
   making, with the one or more physical computer processors, an automatic adjustment to the pressurized flow of breathable gas to enhance the comfort level of the subject, the automatic adjustment based on the received feedback information and the output signals, the automatic adjustment including adjustment of one or more of the pressure generator or the humidifier;
   receiving, with the user interface, additional feedback information entered and/or selected through the user interface subsequent to the automatic adjustment; and
   prompting, with the one or more physical computer processors, the subject to manually adjust one or more of the pressure generator, the humidifier, or an ambient environment based on the additional feedback information.

8. The method of claim 7, wherein the pressure support system further comprises a subject interface configured to deliver the pressurized flow of breathable gas to the airway of the subject,
   wherein the method further comprises controlling, with the one or more physical computer processors, the subject interface, the pressure generator, and the humidifier to deliver the pressurized flow of breathable gas to the subject according to the predetermined therapy regime based on the output signals,
   wherein the automatic adjustment includes adjustment of one or more of the pressure generator, the humidifier, or the subject interface; and
   prompting, with the one or more physical computer processors, the subject to manually adjust the subject interface based on the additional feedback information.

9. The method of claim 7, wherein the pressure support system further comprises a subject interface configured to deliver the pressurized flow of breathable gas to the airway of the subject that includes a subject interface heater configured to controllably heat the pressurized flow of breathable gas in the subject interface,
   wherein the method further comprises controlling, with the one or more physical computer processors, the subject interface heater, the pressure generator, and the humidifier to deliver the pressurized flow of breathable gas to the subject according to the predetermined therapy regime based on the output signals,
   wherein the automatic adjustment includes adjustment of one or more of the pressure generator, the humidifier, or the subject interface heater; and
   prompting, with the one or more physical computer processors, the subject to manually adjust the subject interface based on the additional feedback information.

10. The method of claim 7, wherein a prompted manual adjustment includes one or more of changing the temperature of the ambient environment, changing a type of therapy of the predetermined therapy regime, or changing physical components of the pressure support system.

11. The method of claim 7, wherein in the user interface includes one or more of a user interface that is integral with the pressure generator or a graphical user interface presented to the subject via a mobile computing device.

12. The method of claim 7, wherein the predetermined therapy regime is based on typical ambient weather conditions during a given season of the year and/or previous feedback information from the subject received during the given season.

13. A pressure support system configured to adjust humidity and/or temperature of a pressurized flow of breathable gas delivered to a subject, the pressure support system comprising:
   means for generating a pressurized flow of breathable gas for delivery to an airway of the subject;
   means for humidifying the pressurized flow of breathable gas;
   means for generating output signals conveying information related to one or more parameters of the pressurized flow of breathable gas;
   means for receiving entry and/or selection of feedback information from the subject indicating a comfort level with the pressurized flow of breathable gas;
   means for controlling the means for generating the pressurized flow of breathable gas and the means for humidifying to deliver the pressurized flow of breathable gas to the subject according to a predetermined therapy regime based on the output signals;
   means for receiving feedback information entered and/or selected through the means for receiving entry and/or selection;
   means for making an automatic adjustment to the pressurized flow of breathable gas to enhance the comfort level of the subject, the automatic adjustment based on the received feedback information and the output signals, the automatic adjustment including adjustment of one or more of the means for generating the pressurized flow of breathable gas or the means for humidifying;

means for receiving additional feedback information entered and/or selected through the means for receiving entry and/or selection subsequent to the automatic adjustment; and means for prompting the subject to manually adjust one or more of the means for generating the pressurized flow of breathable gas, the means for humidifying, or the ambient environment based on the additional feedback information.

14. The system of claim 13, further comprising a means for delivering the pressurized flow of breathable gas to the airway of the subject, wherein the means for controlling controls the means for delivering, the means for generating the pressurized flow of breathable gas, and the means for humidifying to deliver the pressurized flow of breathable gas to the subject according to the predetermined therapy regime based on the output signals, wherein the automatic adjustment includes adjustment of one or more of the means for delivering, the means for generating the pressurized flow of breathable gas, or the means for humidifying; and wherein the means for prompting prompts the subject to manually adjust the means for delivering based on the additional feedback information.

15. The system of claim 13, further comprising a means for delivering the pressurized flow of breathable gas to the airway of the subject that includes means for controllably heating the pressurized flow of breathable gas in the means for delivering, wherein the means for controlling controls the means for controllably heating, the means for generating the pressurized flow of breathable gas, and the means for humidifying to deliver the pressurized flow of breathable gas to the subject according to the predetermined therapy regime based on the output signals, wherein the automatic adjustment includes adjustment of one or more of the means for controllably heating, the means for generating the pressurized flow of breathable gas, or the means for humidifying; and wherein the means for prompting prompts the subject to manually adjust the means for delivering including the means for controllably heating based on the additional feedback information.

16. The system of claim 13, wherein a prompted manual adjustment includes one or more of changing the temperature of the ambient environment, changing a type of therapy of the predetermined therapy regime, or changing physical components of the pressure support system.

17. The system of claim 13, wherein in the means for receiving entry and/or selection includes one or more of means for receiving entry and/or selection that is integral with the pressure generator or means for receiving entry and/or selection presented to the subject via a mobile computing device.

18. The system of claim 13, wherein the predetermined therapy regime is based on typical ambient weather conditions during a given season of the year and/or previous feedback information from the subject received during the given season.

* * * * *